(12) United States Patent
Yoshida et al.

(10) Patent No.: US 6,992,068 B2
(45) Date of Patent: Jan. 31, 2006

(54) CYTOKINE PRODUCTION INHIBITORS, AGENTS FOR PROTECTING AND PROMOTING LIVER FUNCTION, ANTI-INFLAMMATORY AGENTS, IMMUNOSUPPRESSANTS, DRUGS, COSMETICS, FOODS AND FOOD MATERIALS

(75) Inventors: Minoru Yoshida, Gifu (JP); Toshihiro Nakayama, Gifu (JP); Hiroichi Nagai, Gifu (JP); Munekazu Iinuma, Gifu (JP)

(73) Assignee: Gifu Shellac Mfg., Co., Ltd., Gifu (JP)

( * ) Notice: Subject to any disclaimer, the term of this patent is extended or adjusted under 35 U.S.C. 154(b) by 358 days.

(21) Appl. No.: 10/311,136

(22) PCT Filed: Jun. 13, 2001

(86) PCT No.: PCT/JP01/05044

§ 371 (c)(1),
(2), (4) Date: Dec. 13, 2002

(87) PCT Pub. No.: WO01/95921

PCT Pub. Date: Dec. 20, 2001

(65) Prior Publication Data

US 2003/0170329 A1 Sep. 11, 2003

(30) Foreign Application Priority Data

Jun. 14, 2000 (JP) .................................... 2000-178478
Nov. 22, 2000 (JP) .................................... 2000-355907

(51) Int. Cl.
*A61K 31/70* (2006.01)

(52) U.S. Cl. .............................................. 514/26; 536/5

(58) Field of Classification Search .................. 514/26; 536/5

See application file for complete search history.

(56) References Cited

U.S. PATENT DOCUMENTS 4,320,225 A * 3/1982 Hashimoto et al. ........ 536/18.1

FOREIGN PATENT DOCUMENTS

| GB | 2019407 | 10/1979 |
| JP | 58-213720 | 12/1983 |
| JP | 8-53360 | 2/1996 |
| JP | 2001-151679 | 6/2001 |

* cited by examiner

*Primary Examiner*—Elli Peselev
(74) *Attorney, Agent, or Firm*—Davis & Bujold P.L.L.C.

(57) ABSTRACT

Highly safe cytokine production inhibitors, agents for protecting and promoting liver function, anti-inflammatory agents and immunosuppressants. Brazilian licorice extract and periandrins, which are constituents thereof, have excellent characteristics of showing effects of inhibiting cytokine production and protecting and promoting liver function, an anti-inflammatory effect and an immunosuppressive effect without any harmful side effects. Thus use of Brazilian licorice extract or periandrins as cytokine production inhibitors makes it possible to inhibit inflammations in various diseases such as rheumatoid arthritis. These substances are also usable as agents for protecting and promoting liver function, anti-inflammatory agents and immunosuppressants. Moreover, foods, cosmetics, sweeteners and food materials containing Brazilian licorice extract exert the effects as described above.

3 Claims, 8 Drawing Sheets

CYTOKINE PRODUCTION INHIBITORS, AGENTS FOR PROTECTING AND PROMOTING LIVER FUNCTION, ANTI-INFLAMMATORY AGENTS, IMMUNOSUPPRESSANTS, DRUGS, COSMETICS, FOODS AND FOOD MATERIALS

TECHNICAL FIELD OF THE INVENTION

This invention relates to cytokine production inhibitors, agents for protecting and promoting liver function, anti-inflammatory agents, immunosuppressants, drugs, cosmetics, foods, and food materials.

BACKGROUND OF THE INVENTION

Inflammation by autoimmune diseases like rheumatism, allergies and atopies is promoted by production of migration enhancement factors of leukocytes called cytokine.

In order to inhibit such cytokine production, steroids such as prednisolone have been conventionally used.

However, steroids have strong side effects. Therefore, repeated administration of the same is difficult.

To make matters worse, there is no report on any component of edible plants and galenicals which shows strong effect of inhibiting cytokine production even at the basic research level.

In short, hardly any medical agent has been existed which can inhibit cytokine production without any side effects, and such an agent has been expected to be discovered.

Licorice (leguminous perennial herb) and glycyrrhizin which is a component thereof have been used for an anti-inflammatory agent, anti-allergic agent and agent for protecting liver function, which promote detoxication and tissue recovery.

However, since glycyrrhizin inhibits corticosteroid metabolism, pseudoaldosteronism (edema with sodium retention, hypertension) may be developed as a side effect.

Therefore, a licorice cannot be administered over a long period to a patient having kidney diseases or hypertension.

Accordingly, a medical agent which is as effective as licorice but which does not develop any side effect has been expected.

SUMMARY OF THE INVENTION

One object of the present invention is to provide a medical agent which exerts effects of inhibiting cytokine production, protecting and promoting liver function, an anti-inflammatory effect, and an immunosuppressive effect, and which hardly causes any side effect. Another object of the present invention is to provide drugs, cosmetics, foods, and food materials to which the aforementioned medical agent is applied.

Heretofore, periandrins and periandradulcins have been reported as main components of a Brazilian licorice. These are both glycosides structurally similar to glycyrrhizin which is a component of a licorice, and are expected to act similar to glycyrrhizin. However, hardly any report has been made in relation to their physiological activities.

The inventors discovered that Brazilian licorice extract and periandrins, which are constituents thereof, have an anti-inflammatory effect and an immunosuppressive effect, and accomplished the present invention.

Brazilian licorice extract is, for example, obtained using extraction vehicles such as ethyl alcohol.

The invention provides a cytokine production inhibitor comprising periandrins as an active ingredient.

Since the periandrins show an effect of inhibiting cytokine production, the cytokine production inhibitor of the present invention inhibits cytokine production and acts as an anti-inflammatory agent.

Accordingly, the cytokine production inhibitor of the present invention can inhibit inflammation developed by cell disorders (for example, by bacteria, toxic elements in medicine and alcohol), autoimmune diseases (such as rheumatism (rheumatoid arthritis, for example), systemic lupus erythematosus, collagenosis, etc.), atopies, allergies, and pollinosis.

Furthermore, periandrins do not inhibit activation of 11 β-hydroxysteroid dehydrogenase.

If activation of 11 β-hydroxysteroid dehydrogenase is inhibited, corticosteroid metabolism is also inhibited, resulting in that pseudoaldosteronism (edema with sodium retention, hypertension) may occur.

Accordingly, the cytokine production inhibitor of the present invention comprising periandrins does not cause pseudoaldosteronism and can be administered, for example, even to a patient having kidney diseases and hypertension over a long period.

The cytokine production inhibitor of the present invention can be produced by compounding periandrins obtained by separating a component held by adsorption chromatography carrier from the Brazilian licorice extract, for example.

In this case, since polysaccharide contained in the Brazilian licorice extract is not entered into the cytokine production inhibitor, it is difficult for the cytokine production inhibitor to get moldy.

Examples of the aforementioned periandrins are periandrin I (PD-I), periandrin II (PD-II), periandrin III (PD-III), periandrin IV (PD-IV), etc.

Cytokine is a cellular glycoprotein, and an endogenous substance in vivo which acts on the other cells. It is a general term for interleukin, interferon, lymphokine, monokine, and tumor necrosis factors.

When cells are damaged by bacteria, toxic elements in medicine, alcohol, etc., or in case of autoimmune diseases such as rheumatism, collagenosis, etc., phagocyte such as macrophage, etc. is activated and autopepsia occurs, resulting in that inflammation is developed. At the same time, cytokine which is a type of migration enhancement factors of leukocytes is produced. However, cytokine has a number of factors which accelerates immunoreaction. Therefore, if cytokine is produced in a large amount, it accelerates aggregation of phagocyte and further worsens the inflammation.

The invention provides a cytokine production inhibitor containing one of Brazilian licorice extract and one or more constituents contained in the extract as an active ingredient.

The cytokine production inhibitor of the present invention contains an extract, or one or more constituents contained in the same, obtained by filtering and drying the liquid extracted from a dried rootstalk of a Brazilian licorice with alcohol.

Brazilian licorice extract inhibits cytokine production, and thus the cytokine production inhibitor of the present invention inhibits cytokine production and serves as an anti-inflammatory agent.

Inflammation which is a symptom of diseases such as cell disorders (for example, by bacteria, toxic elements in medicine and alcohol), autoimmune diseases (such as rheumatism (rheumatoid arthritis, for example), systemic lupus erythematosus, collagenosis, etc.), atopies, allergies, and pollinosis is in many cases accelerated by cytokine. Consequently, the cytokine production inhibitor of the present invention inhibits inflammation by the aforementioned diseases.

Brazilian licorice extract, in addition, is on the list of food additives in Japan as a sweetener, and is superior in that it develops no harmful side effect.

The invention provides the cytokine production inhibitor one or more constituents of the aforementioned comprise periandrins.

The cytokine production inhibitor of the present invention inhibits cytokine production due to periandrins contained in Brazilian licorice extract.

Accordingly, the cytokine production inhibitor of the present invention, inhibits inflammation developed by cell disorders, autoimmune diseases, atopies, allergies, and pollinosis, which may be worsened by cytokine.

This cytokine production inhibitor does not inhibit activation of 11 β-hydroxysteroid dehydrogenase, and thus does not cause pseudoaldosteronism and can be administered, for example, to a patient having kidney diseases and hypertension, over a long period.

Furthermore, this cytokine production inhibitor has no harmful side effect. Therefore, it can be administered over a long period in treatment of autoimmune diseases and after organ transplant, for example, without developing any side effect unlike the conventional steroids.

The invention provides drugs comprising the cytokine production inhibitor as an anti-inflammatory, anti-allergic, or anti-atopic active ingredient.

The drugs of the present invention comprise periandrins, Brazilian licorice extract, or one or more constituents of the extract. Therefore, it inhibits cytokine production and eases symptoms of inflammation, allergy, atopy, and pollinosis.

The drugs of the present invention are also advantageous in that they have no side effect.

The drugs of the present invention can be taken as oral medicine, external preparations, injectable solutions, vaparole, nose drops, eye drops, etc., for example.

The drugs of the present invention can be in the form of pill or tablet, liquid, injectable solution, ointment, cream, lotion, aerosol, suppository, etc., for example.

The drugs of the present invention can compounded with other ingredients which show an anti-inflammatory effect, an anti-allergic effect, or an anti-atopic effect.

The invention provides cosmetics comprising the cytokine production inhibitor as an anti-inflammatory, anti-allergic, or anti-atopic active ingredient.

The cosmetics of the present invention comprise periandrins, Brazilian licorice extract, or one or more constituents of the extract. Therefore, it inhibits cytokine production and eases symptoms of inflammation, allergy, atopy, and pollinosis.

Accordingly, use of the cosmetics of the present invention can improve itches and pains on the skin by allergic symptoms and inflammation. The cosmetics of the present invention can be used even by an atopic person.

The cosmetics of the present invention are also advantageous in that they have no side effect.

The cosmetics of the present invention can be in the form of cream, ointment, lotion, milky lotion, solid body, powder, etc., for example.

Examples of the cosmetics of the present invention are basic skin care products such as lotion, milky lotion, essence, moisturizing cream, etc., sun protection products such as sunscreen cream, sunscreen lotion, sunscreen oil, carmine lotion, etc., makeups such as foundation, eye liner, mascara, eye shadow, blush-on for cheeks, lipstick, etc., cleansers such as facial wash, body shampoo, hair shampoo, etc, perfumes, antiperspirant deodorants, etc.

The invention provides foods comprising the cytokine production inhibitor as an anti-inflammatory, anti-allergic, or anti-atopic active ingredient.

The foods of the present invention contain periandrins, Brazilian licorice extract, or one or more constituents of the extract. Therefore, it inhibits cytokine production and eases symptoms of inflammation, allergy, atopy, and pollinosis.

Accordingly, an intake of the foods of the present invention can improve various inflammatory symptoms by atopy, pollinosis, etc., for example.

The foods of the present invention are also advantageous in that they have no side effect.

The foods of the present invention can be made into oral compositions such as tea, soft drinks, gums, candies, etc., pastes of marine products such as steamed fish pastes, fish sausages, etc., stock farm products such as sausages, hams, etc., Western-style confectionery, Japanese-style confectionery, noodles such as raw noodles, noodles for boiling, etc., seasonings such as sauces, soy sauces, dips, etc., and general food products such as pickles, prepared foods, etc.

The foods of the present invention can, as far as the effect of the present invention is not deteriorated, compound various ingredients generally used in foods, such as sugar, condensed milk, wheat flour, shortening, salt, glucose sugar, chicken eggs, butter, margarine, starch syrup, calcium, iron, vitamins, seasonings, spices, etc.

The invention provides food materials comprising the cytokine production inhibitor as an anti-inflammatory, anti-allergic, or anti-atopic active ingredient.

The food materials of the present invention comprise periandrins, Brazilian licorice extract, or one or more constituents of the extract. Therefore, it inhibits cytokine production and eases symptoms of inflammation, allergy, atopy, and pollinosis.

Accordingly, an intake of foods compounding the food materials of the present invention can improve various inflammatory symptoms by atopy, pollinosis, etc., for example.

The food materials of the present invention are also advantageous in that they have no side effect.

The food materials of the present invention can be a sweetener, for example.

The food materials of the present invention can compound various ingredients generally used in foods (like sugar, condensed milk, wheat flour, shortening, salt, glucose sugar, chicken eggs, butter, margarine, starch syrup, calcium, iron, vitamins, seasonings, spices, etc.).

The food materials of the present invention can be added to various foods and drinks (like oral compositions such as tea, soft drinks, gums, candies, etch, pastes of marine products such as steamed fish pastes, fish sausages, etc., stock farm products such as sausages, hams, etc., Western-style confectionery, Japanese-style confectionery, noodles such as raw noodles, noodles for boiling, etc., seasonings such as sauces, soy sauces, dips, etc., and general food products such as pickles, prepared foods, etc.).

The invention provides an agent for protecting and promoting liver function comprising periandrins as an active ingredient.

The periandrins show an effect of protecting and promoting liver function, and thus the agent for protecting and promoting liver function, comprising periandrins as an active ingredient, of the present invention has also an effect of protecting and promoting liver function.

Cytokine is produced in case that there are any liver disorders. However, the agent for protecting and promoting liver function of the present invention inhibits cytokine production by protecting and promoting liver function and eases symptoms of inflammation, allergy, atopy, and pollinosis, for example.

Accordingly, the agent for protecting and promoting liver function of the present invention is as effective as the conventionally used licorice extract, and more advantageously, it has no side effect unlike licorice.

Therefore, the agent for protecting and promoting liver function of the present invention can be administered over a long period, for example, to a patient who has kidney diseases and hypertension and to whom long-term administration of licorice is not possible.

The agent for protecting and promoting liver function of the present invention can compound periandrins separated and purified from Brazilian licorice extract, for example. In this case, since polysaccharide contained in Brazilian licorice extract is not entered into the agent for protecting and promoting liver function, it is difficult for the agent for protecting and promoting liver function to get moldy.

Examples of the aforementioned periandrins are periandrin I (PD-I), periandrin II (PD-II), periandrin III (PD-III), periandrin IV (PD-IV), etc.

The invention provides an agent for protecting and promoting liver function comprising one of Brazilian licorice extract and one or more constituents contained in the extract as an active ingredient.

The agent for protecting and promoting liver function of the present invention comprises extract, or one or more constituents contained in the same, obtained by filtering and drying liquid extracted from a dried rootstalk of a Brazilian licorice with alcohol.

Brazilian licorice extract shows an effect of protecting and promoting liver function, and thus the agent for protecting and promoting liver function, comprising Brazilian licorice extract as an active ingredient, of the present invention is also effective in protecting and promoting of liver function.

Cytokine is produced in case that there are any liver disorders. However, the agent for protecting and promoting liver function of the present invention inhibits cytokine production by protecting and promoting liver function and eases symptoms of inflammation, allergy, atopy, and pollinosis, for example.

Accordingly, the agent for protecting and promoting liver function of the present invention is as effective as the conventionally used licorice extract. More advantageously, it has no side effect unlike licorice.

Therefore, the agent for protecting and promoting liver function of the present invention can be administered over a long period, for example, to a patient who has kidney diseases and hypertension and to whom long-term administration of licorice is not possible.

The invention provides the agent for protecting and promoting liver function one or more constituents of the aforementioned comprise periandrins.

The agent for protecting and promoting liver function of the present invention comprises periandrins contained in the extract as an active ingredient.

Therefore, this agent for protecting and promoting liver function, inhibits cytokine production by protecting and promoting liver function and eases symptoms of inflammation, allergy, atopy, and pollinosis, for example.

Also this agent for protecting and promoting liver function has no side effect (such as pseudoaldosteronism).

Therefore, it can be administered over a long period, for example, to a patient who has kidney diseases and hypertension and to whom long-term administration of licorice is not possible.

The invention provides drugs comprising the agent for protecting and promoting liver function as an active ingredient for protecting and promoting liver function.

The drugs of the present invention comprise periandrins, Brazilian licorice extract, or one or more constituents contained in the extract. Thus, they have an effect of protecting and promoting liver function.

Also, the drugs of the present invention inhibit cytokine production by protecting and promoting liver function and ease symptoms of inflammation, allergy, atopy, and pollinosis, for example.

The drugs of the present invention are also advantageous in that they have no harmful side effect.

The drugs of the present invention, as well as the drugs can be made into various forms and compounded with other ingredients.

The invention provides foods comprising the agent for protecting and promoting liver function as an active ingredient for protecting and promoting liver function.

The foods of the present invention comprise periandrins, Brazilian licorice extract, or one or more constituents contained in the extract. Thus, they have effect of protecting and promoting liver function.

Also, the foods of the present invention inhibit cytokine production by protecting and promoting liver function and ease symptoms of inflammation, allergy, atopy, and pollinosis, for example.

Accordingly, an intake of the foods of the present invention can protect and promote liver function and improve various inflammatory symptoms by atopy, pollinosis, etc., for example.

The foods of the present invention are also advantageous in that they have no harmful side effect.

The foods of the present invention, can be made into various forms and compounded with other ingredients.

The invention provides food materials comprising the agent for protecting and promoting liver function as an active ingredient for protecting and promoting liver function.

The food materials of the present invention comprise periandrins, Brazilian licorice extract, or one or more constituents contained in the extract. Thus, they have an effect of protecting and promoting liver function.

Also, the food materials of the present invention inhibit cytokine production by protecting and promoting liver function and ease symptoms of inflammation, allergy, atopy, and pollinosis, for example.

Accordingly, an intake of foods compounding the food materials of the present invention can protect and promote liver function and improve various inflammatory symptoms by atopy, pollinosis, etc., for example.

The foods of the present invention are also advantageous in that they have no harmful side effect.

The food materials of the present invention can be a sweetener, for example.

The food materials of the present invention, can be compounded with various ingredients and can be added to various foods.

The invention provides an anti-inflammatory agent comprising periandrins as an active ingredient.

The anti-inflammatory agent of the present invention comprise periandrins, and thus, it shows an anti-inflammatory effect.

Particularly, the anti-inflammatory agent of the present invention can reduce inflammation due to autoimmune diseases (such as rheumatism (rheumatoid arthritis, for example), systemic lupus erythematosus, couagenosis, multiple sclerosis, and atopies) by inhibiting cytokine production.

The anti-inflammatory agent of the present invention is also advantageous in that they have no harmful side effect. Therefore, it can be administered over a long period in treatment of autoimmune diseases and after organ transplant, for example, without developing any side effect unlike the conventional steroids.

The anti-inflammatory agent of the present invention can compound periandrins separated and purified from Brazilian licorice extract, for example. In this case, since polysaccharide contained in Brazilian licorice extract is not entered into the agent for protecting and promoting liver function, it is difficult for the agent for protecting and promoting liver function to get moldy.

Examples of the aforementioned periandrins are periandrin I (PD-I), periandrins II (PD-II), periandrin III (PD-III), periandrin IV (PD-IV), etc.

The invention provides an anti-inflammatory agent comprising one of Brazilian licorice extract and one or more constituents contained in the extract as an active ingredient.

The anti-inflammatory agent of the present invention comprises the extract, or one or more constituents contained in the same, and thus, it shows an anti-inflammatory effect.

Particularly, the anti-inflammatory agent of the present invention can reduce inflammation due to autoimmune diseases (such as rheumatism (rheumatoid arthritis, for example), systemic lupus erythematosus, collagenosis, multiple sclerosis, and atopies) by inhibiting cytokine production.

The anti-inflammatory agent of the present invention is also advantageous in that they have no harmful side effect. Therefore, it can be administered over a long period in treatment of autoimmune diseases and after organ transplant, for example, without developing any side effect unlike the conventional steroids.

Examples of the aforementioned one or more constituents are triterpenoid glycosides and triterpenoid aglycones, such as periandrins I, II, III, IV and V, periandradulcins A, B and C, and aglycones of the aforementioned. In short, they are triterpenoid glycosides and/or triterpenoid aglycones contained in Brazilian licorice extract.

The invention provides the anti-inflammatory agent one or more constituents of the aforementioned comprise periandrins.

The anti-inflammatory agent of the present invention comprises periandrins contained in Brazilian licorice extract, and thus, it shows an anti-inflammatory effect.

Also, the anti-inflammatory agent of the present invention, can reduce inflammation due to autoimmune diseases (such as rheumatism (rheumatoid arthritis, for example), systemic lupus erythematosus, collagenosis, multiple sclerosis, and atopies) by inhibiting cytokine production.

The anti-inflammatory agent of the present invention is also advantageous in that they have no harmful side effect. Therefore, it can be administered over a long period in treatment of autoimmune diseases and after organ transplant, for example, without developing any side effect unlike the conventional steroids.

The invention provides an immunosuppressant comprising periandrins as an active ingredient.

Also, the immunosuppressant, comprising periandrins, of the present invention can ease symptoms of autoimmune diseases (caused by abnormality in human immune system mistaking cells or tissues of itself for antigens due to genetic predisposition and low molecular extrinsic factor called hapten (such as, rheumatism (rheumatoid arthritis, for example), systemic lupus erythematosus, collagenosis, multiple sclerosis, and atopies).

Specifically, this autoimmune agent is unlikely to cause aggravation (i.e. rebound) of the symptoms after the administration is stopped.

Additionally, since the autoimmune agent of the present invention, has no harmful side effect, it can be administered over a long period.

The autoimmune agent of the present invention can compound periandrins separated and purified from Brazilian licorice extract, for example. In this case, since polysaccharide contained in Brazilian licorice extract is not entered into the agent for protecting and promoting liver function, it is difficult for the agent for protecting and promoting liver function to get moldy.

Examples of the aforementioned periandrins are periandrin I (PD-I), periandrins II (PD-II), periandrin III (PD-III), periandrin IV (PD-IV), etc.

The invention provides an immunosuppressant comprising one of Brazilian licorice extract and one or more constituents contained in the extract as an active ingredient.

The immunosuppressant, comprising one of Brazilian licorice extract and one or more constituents contained in the extract, of the present invention can ease symptoms of autoimmune diseases (caused by abnormality in human immune system mistaking cells or tissues of itself for antigens due to genetic predisposition and low molecular extrinsic factor called hapten (such as, rheumatism (rheumatoid arthritis, for example), systemic lupus erythematosus, collagenosis, multiple sclerosis, and atopies).

Also, the autoimmune agent of the present invention has no harmful side effect, and thus it can be administered over a long period.

Examples of the aforementioned one or more constituents are triterpenoid glycosides and triterpenoid aglycones, such as periandrins I, II, III, IV and V, periandradulcins A, B and C, and aglycones of the aforementioned. In short, they are triterpenoid glycosides and/or triterpenoid aglycones comprised in Brazilian licorice extract.

The invention provides the autoimmune agent and one or more constituents of the aforementioned comprise periandrins.

The immunosuppressant, comprising periandrins as one or more constituents contained in Brazilian licorice extract, of the present invention can ease symptoms of autoimmune diseases (caused by abnormality in human immune system mistaking cells or tissues of itself for antigens due to genetic predisposition and low molecular extrinsic factor called hapten (for example, rheumatism (such as rheumatoid arthritis), systemic lupus erythematosus, collagenosis, multiple sclerosis, and atopies).

Also, the autoimmune agent of the present invention, has no harmful side effect, and thus it can be administered over a long period.

The invention provides drugs comprising the anti-inflammatory agent as an anti-inflammatory active ingredient.

The drugs of the present invention comprise periandrins, Brazilian licorice extract, or one or more constituents contained in the extract. Thus, they have an anti-inflammatory effect.

Particularly, the drugs of the present invention reduce inflammation due to autoimmune diseases (such as rheumatism (rheumatoid arthritis, for example), systemic lupus erythematosus, collagenosis, multiple sclerosis, and atopies).

The anti-inflammatory agent of the present invention is also advantageous in that it has no harmful side effect.

The drugs of the present invention, can be made into various forms and compounded with other ingredients.

The invention provides cosmetics containing the anti-inflammatory agent as an anti-inflammatory active ingredient.

The cosmetics of the present invention comprise periandrins, Brazilian licorice extract, or one or more constituents of the extract. Therefore, they have an anti-inflammatory effect (i.e. effect by which inflammation due to autoimmune diseases such as rheumatism (rheumatoid arthritis, for example), systemic lupus erythematosus, collagenosis, multiple sclerosis, and atopies is reduced).

Accordingly, use of the cosmetics of the present invention can reduce inflammation caused by the aforementioned symptoms.

The cosmetics of the present invention are also advantageous in that they have no side effect.

The cosmetics of the present invention, can be made into various forms and products.

The invention provides foods comprising the anti-inflammatory agent as an anti-inflammatory active ingredient.

The foods of the present invention comprise periandrins, Brazilian licorice extract, or one or more constituents contained in the extract. Therefore, they have an anti-inflammatory effect (i.e. effect by which inflammation due to autoimmune diseases such as rheumatism (rheumatoid arthritis, for example), systemic lupus erythematosus, collagenosis, multiple sclerosis, atopies, etc. is reduced).

Accordingly, an intake of the foods of the present invention, for example, can reduce inflammation due to the aforementioned symptoms.

The foods of the present invention are also advantageous in that they have no harmful side effect.

The foods of the present invention, can be made into various forms and compounded with other ingredients.

The invention provides food materials comprising the anti-inflammatory agent as an anti-inflammatory active ingredient.

The food materials of the present invention comprise periandrins, Brazilian licorice extract, or one or more constituents contained in the extract. Therefore, they have an anti-inflammatory effect (i.e. effect by which inflammation due to autoimmune diseases such as rheumatism (rheumatoid arthritis, for example), systemic lupus erythematosus, collagenosis, multiple sclerosis, atopies, etc. is reduced).

Accordingly, an intake of the food materials of the present invention, for example, can reduce inflammation due to the aforementioned symptoms.

The food materials of the present invention can be a sweetener, for example.

The food materials of the present invention, can be compounded with various ingredients and can be added to various foods.

The invention provides drugs comprising the immunosuppressant as an immunosuppressive active ingredient.

The drugs of the present invention comprise periandrins, Brazilian licorice extract, or one or more constituents contained in the extract. Thus, they have an immunosuppressive effect.

Accordingly, the drugs of the present invention reduce development of autoimmune diseases (such as rheumatism (rheumatoid arthritis, for example), systemic lupus erythematosus, collagenosis, multiple sclerosis, and atopies) and also ease the symptoms thereof.

The immunosuppressant of the present invention is also advantageous in that it has no harmful side effect.

The drugs of the present invention, can be made into various forms and compounded with other ingredients.

The invention provides cosmetics comprising the immunosuppressant as an immunosuppressive active ingredient.

The cosmetics of the present invention comprise periandrins, Brazilian licorice extract, or one or more constituents of the extract. Therefore, they have an immunosuppressive effect.

Accordingly, use of the cosmetics of the present invention can reduce development of autoimmune diseases such as rheumatism (rheumatoid arthritis, for example), systemic lupus erythematosus, collagenosis, multiple sclerosis, and atopies, and ease the symptoms thereof.

The cosmetics of the present invention are also advantageous in that they have no side effect.

The cosmetics of the present invention, can be made into various forms and products.

The invention provides foods comprising the immunosuppressant as an immunosuppressive active ingredient.

The foods of the present invention comprise periandrins, Brazilian licorice extract, or one or more constituents contained in the extract. Therefore, they have an immunosuppressive effect.

Accordingly, an intake of the foods of the present invention, for example, can reduce development of autoimmune diseases such as rheumatism (rheumatoid arthritis, for example), systemic lupus erythematosus, collagenosis, multiple sclerosis, atopies) and ease the symptoms thereof.

The foods of the present invention are also advantageous in that they have no harmful side effect.

The foods of the present invention, as well as the foods can be made into various forms and compounded with other ingredients.

The invention provides food materials comprising the immunosuppressant as an immunosuppressive active ingredient.

The food materials of the present invention comprise periandrins, Brazilian licorice extract, or one or more constituents contained in the extract. Therefore, they have an immunosuppressive effect.

Accordingly, an intake of the food materials of the present invention, for example, can reduce development of autoimmune diseases such as rheumatism (rheumatoid arthritis, for example), systemic lupus erythematosus, collagenosis, multiple sclerosis, atopies)

and ease the symptoms thereof.

The food materials of the present invention can be a sweetener, for example.

The food materials of the present invention, can compound with various ingredients and can be added to various foods.

DETAILED DESCRIPTION OF THE PREFERRED EMBODIMENTS

Figure 1:
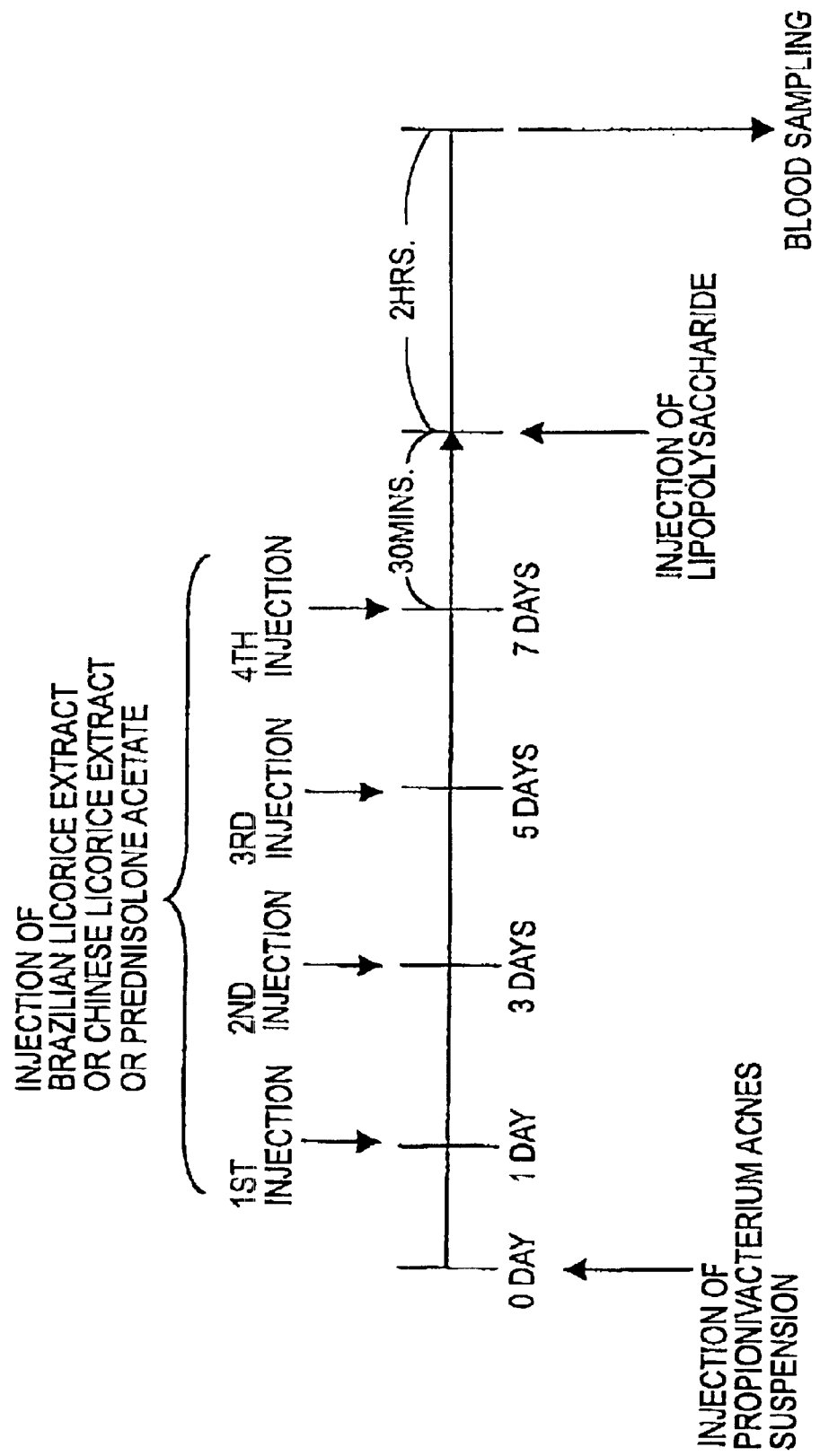
FIG. 1 is an explanatory diagram of an experimentation method according to an experiment 1.

Cytokine production inhibitors, agents for protecting and promoting liver function, anti-inflammatory agents, immunosuppressants, drugs, cosmetics, foods, and food materials according to the present invention will now be explained below.

a) Firstly, extract, etc. obtained in examples and comparative examples are described.

EXAMPLE 1

Brazilian licorice extract was obtained using the following steps I–V. These steps were repeated three times.

I. 300 g of dried rootstalk of Brazilian licorice was ground, and then, extraction was performed for an hour with 900 g of 30 wt % ethanol at the circumfluent temperature.

II. The liquid extract obtained in step I was suctioned and filtered, and then, solid-liquid separation was performed.

III. The solid material obtained in step II was again ground and extraction was performed as in step I, and then the obtained liquid extract was separated as in step II.

IV. The solid material obtained in step III was again ground and extraction was performed as in step I, and then the obtained liquid extract was separated as in step II.

V. All the liquid extracts obtained in steps I, III and IV were collected together, vacuumed and concentrated, and then dried by spray-drying to obtain solid extract.

Average yield and standard deviation of the last extract obtained in the above manner were, respectively, 1.03 g and 0.49 g.

This Brazilian licorice extract, as can be understood from the later described experiments, has effects of inhibiting cytokine production and protecting and promoting liver function. Accordingly, this Brazilian licorice extract can be used as cytokine production inhibitors, agents for protecting and promoting liver function, drugs, cosmetics, foods, and food materials.

EXAMPLE 2

The extraction method of Example 1 was exercised in basically the same manner to obtain Brazilian licorice extract. However, in this case, 900 g of 20 wt % ethanol was used in place of 900 g of 30 wt % ethanol for extraction.

Average yield and standard deviation of the extract obtained in the above manner were, respectively, 1.53 g and 2.11 g.

This Brazilian licorice extract, as can be understood from the later described experiments, has an anti-inflammatory effect and an immunosuppressive effect. Accordingly, this Brazilian licorice extract can be used as anti-inflammatory agents, immunosuppressants, drugs, cosmetics, foods, and food materials.

EXAMPLE 3

Brazilian licorice extract obtained in Example 2 was fractionated using the following steps I–IV.

I. 575 g of Brazilian licorice extract was dissolved in a 20 v/v % methanol solution, and introduced into a column (300×400 mm) which was filled with ion-exchange resin (DIAION HP-20, produced by Mitsubishi Chemical Corporation), to be suctioned and cleaned with a 20 v/v % methanol solution.

II. The cleaning component obtained in step I was dried under reduced pressure, and 106 g of a solid content (BL. 1) was thus obtained.

III. The column is cleaned with a 50 v/v % methanol solution, and by drying under reduced pressure the resulted cleaning solution, 63.4 g of a solid content (BL. 2) was obtained.

IV. The column is cleaned with 80 v/v % methanol solution, and by drying under reduced pressure the resulted cleaning solution, 296 g of a solid content (BL. 3) was obtained.

In order to prove that periandrins are contained in the BL. 3, the following method was used.

Particularly, purified periandrins obtained in later described Experiment 4 were made a preparation. Periandrins were identified through silica gel thin-layer chromatography using two types of developing solvents (one of which contains chloroform, methanol, water and acetic acid in the proportions of 70:35:5:5; and the other of which contains ethyl acetate, isopropyl alcohol, water, ethanol and diethylamine in the proportions of 20:10:8:1:0.3).

The BL. 3 (which is a constituent contained in Brazilian licorice extract and which contains periandrins) has an excellent immunosuppressive effect as seen in the later explained Experiment 4.

EXAMPLE 4

From the extract obtained in Example 1 or 2, purified periandrins (PD-I, PD-II, PD-III and PD-IV) were obtained by way of the usual separation purification method using column chromatography.

Nuclear magnetic resonance spectrum and mass spectrum of the obtained PD-I, PD-II, PD-III and PD-IV were measured respectively, and it was found that each of them is not a mixture.

The periandrins (PD-I, PD-II, PD-III and PD-IV) obtained in Example 4 are, as shown in later explained Experiment 5, hardly inhibits activity of 11 β-hydroxysteroid dehydrogenase.

Therefore, these periandrins do not develop pseudoaldosteronism, which is considered to be caused by inhibition of 11 β-hydroxysteroid dehydrogenase activity.

These penandrins have effects of inhibiting cytokine production and protecting and promoting liver function, an anti-inflammatory effect, and an immunosuppressive effect.

EXAMPLE 5

From Brazilian licorice extract obtained in Example 2, purified periandrins (PD-I, PD-II, PD-III and PD-IV) were obtained using the following steps I–IV.

I. 4-nitrobenzylbromide (produced by Tokyo Kasei Kogyo Co., Ltd.), dimethylformaldehyde as a solvent, and triethylamine as a hydrobromic scavenger were added to Brazilian licorice extract. According to the usual manner, 4-nitrobenzylization was performed.

As a result, 4-nitrobenzylized PD-I, PD-II, PD-III and PD-IV were obtained.

II. After the 4-nitrobenzylization in step I, dimethylformaldehyde was vacuumed and distilled, to extract a reaction product containing 4-nitrobenzylized PD-I, PD-II, PD-III and PD-IV with ethyl acetate.

III. From the ethyl acetate extract obtained in step II, the 4-nitrobenzylized PD-I, PD-II, PD-III and PD-IV were separated and purified through chromatography with silica gel (WAKOGEL C-200, produced by Wako Pure Chemical Industries,Ltd.) and octadecylsilane (produced by Chromatorex, Fuji Silysia Chemical Ltd.).

IV. The 4-nitrobenzylized PD-I, PD-II, PD-III and PD-IV obtained in step II were dissolved in an acetic solvent, and then, by adding zinc powder, denitrobenzilized reaction was performed to obtain purified periandrins (PD-I, PD-II, PD-III and PD-IV).

The periandrins obtained in Example 5 are, like the periandrins obtained in Example 4, hardly inhibits activity of 11 β-hydroxysteroid dehydrogenase and thus do not develop pseudoaldosteronism.

Furthermore, the periandrins obtained in Example 4 or 5 have, as can be clearly seen from later explained Experiment 6, effects of inhibiting cytokine production and protecting and promoting liver function, an anti-inflammatory effect and an immunosuppressive effect.

Comparative Example 1

Chinese licorice extract was obtained in the same manner as in the aforementioned Example 1.

Chinese licorice is a typical species of licorice, which has been used as an agent for protecting liver function.

Average yield and standard deviation of the extract obtained in the above manner were, respectively, 27.0 g and 1.03 g.

Comparative Example 2

Chinese licorice extract was obtained in the same manner as the aforementioned Example 2.

Average yield and standard deviation of the extract obtained in the above manner were, respectively, 28.5 g and 2.18 g.

b) Secondly, experiments conducted to confirm the effects of the extract obtained in the aforementioned Examples are explained.

Experiment 1

The following experiment was performed to examine the effects of inhibiting cytokine production and lowering GOT activity of the extracts obtained in Example 1 and Comparative Example 1. The experiment procedures are shown in FIG. 1.

I. Preparation of Mice to be Used in the Experiment

Male mice of ddy system (Japan SLC, Inc.), each of which weighs 18–20 g, are prepared for the experiment. The mice are divided into six groups, namely, A, B, C, D, E and F, each consisting of eight mice.

II. Injection of Propionivacterium Acnes Suspension 5 mg of Propionivacterium acnes suspension was injected into the vein of the aforementioned mice respectively, to cause hepatopathy.

III. Injection of Brazilian Licorice Extract and Comparative Sample

A solvent without drugs was injected into the mice in group A.

Brazilian licorice extract obtained in Example 1 was injected into the abdominal cavity of the mice in groups B and C four times in total, that is, one day, three days, five days and seven days after the injection of the propionivacterium acnes suspension in step II. The dosage per one injection was 25 mg, respectively.

Chinese licorice extract obtained in Comparative Example 1 was injected into the abdominal cavity of the mice in groups D and E four times in total, that is, one day, three days, five days and seven days after the injection of the propionivacterium acnes suspension in step II. The dosage per one injection was 25 mg, respectively.

5 mg of prednisolone acetate was injected into the abdominal cavity of the respective mice in group F four times in total, that is, one day, three days, five days and seven days after the injection of the propionivacterium acnes suspension in step II.

Prednisolone acetate is a typical type of prednisolone, which has been used as a cytokine production inhibitor.

IV. Sampling of Blood

10 μg of lipopolysaccharide was injected into the vein of the mice in all groups respectively, thirty minutes after the fourth injection in step II (as to the mice in group A, the injection was performed at the same timing as the mice in the other groups). Then, two hours later, blood was taken from all the mice to obtain serum. There was no visible change in weight and food and water consumption of the mice.

V. Measurement of Cytokine in Blood

From the serum obtained in step III, measurement of interleukin-6 (IL-6), which is a kind of cytokine, was performed.

For the measurement, a commercially available measurement kit which adopts Fluorescence Linked immuno-Sorbent Assay using fluorescence labeling antibody was used.

VI. Measurement of GOT in Blood

From the serum obtained in step III, glutamic-oxaloacetic transaminase activity (GOT) was measured.

For the measurement, a commercially available measurement kit which adopts Enzyme Linked immuno-Sorbent Assay using enzyme labeling antibody was used.

Blood cytokine (IL-6) levels of the respective eight mice were measured per each of the groups A–F. Table 1 shows the average yield and standard deviation.

The measured values in Table 1 show IL-6 levels (unit: picogram) per 1 ml serum.

TABLE 1

| Group | Average of eight mice | Standard deviation |
|---|---|---|
| A | 360349 | 93784 |
| B | 40845 | 11348 |
| C | 76772 | 58125 |
| D | 280986 | 97265 |
| E | 191646 | 91081 |
| F | 26473 | 15300 |

As shown in Table 1, the blood IL-6 levels of the mice in groups B and C to which Brazilian licorice extract was injected were remarkably reduced compared to the blood IL-6 levels of the mice in group A without drug injection and of the mice in groups D and E to which Chinese licorice extract was injected. The levels were rather close to the blood IL-6 levels of group F to which prednisolone acetate was injected.

In view of the above, it is clear that Brazilian licorice extract has an effect of inhibiting cytolkine production which equals to the effect by prednisolone acetate.

Table 2 shows average yield and standard deviation of blood GOT activity levels of the respective eight mice measured per each of the groups A–F.

The measured values in Table 2 are shown in Kermen Units.

TABLE 2

| Group | Average of eight mice | Standard deviation |
|---|---|---|
| A | 918.160 | 256.863 |
| B | 244.359 | 31.405 |
| C | 201.840 | 18.893 |
| D | 462.386 | 118.867 |
| E | 412.544 | 159.981 |
| F | 350.705 | 68.166 |

As can be seen in Table 2, the blood GOT activity levels of the mice in groups B and C to which Brazilian licorice extract was injected were lower than the blood GOT activity levels of any other groups.

In view of the above, Brazilian licorice extract has a superior effect of protecting and promoting liver function to Chinese licorice extract or prednisolone acetate.

Experiment 2

Anti-inflammatory effect and immunosuppressive effect of the extract obtained in Example 2 and Comparative Example 2 were examined by means of collagen induction arthritis model experiment.

I. Preparation of Mice to be Used in Experiment

DBJ/1J mice were used in the experiment. The mice are divided into six groups, namely, G, H, I, J, K and L, each consisting of six mice.

II. Induction of Arthritis by Injection of Emulsion to Mice (Immunity)

An equal amount of 8 mg/ml concentration of a collagen solution (the solvent is phosphate buffered saline containing 0.01 mol/L acetic acid) and fetal bovine serum containing 4 mg/ml concentration of supersonically treated Microbacterium tuberculosis H37Ra were mixed to prepare emulsion.

50 $\mu$l (200 $\mu$g/head) of the emulsion was then injected to the back neck skin of each of the mice under ether (first immunity).

Three weeks after the first immunity, 50 $\mu$l (200 $\mu$g/head) of the emulsion was injected to the tail head skin of each of the mice (second immunity).

Arthritis was induced in the respective mice due to the first and second immunities.

III. Injection of Brazilian Licorice Extract and Comparative Sample to Mice

A solvent without drugs was injected into the mice in group G.

Brazilian licorice extract obtained in Example 2 was diluted by physiological saline so that the dosage is 6 mg/head, and the obtained diluted solution was injected into the abdominal cavity of the mice in group H by 1 ml every other day after the first immunity.

Brazilian licorice extract obtained in Example 2 was diluted by physiological saline so that the dosage is 12.5 mg/head, and the obtained diluted solution was injected into the abdominal cavity of the mice in group I by 1 ml every other day after the first immunity.

Chinese licorice extract obtained in Comparative Example 2 was diluted by physiological saline so that the dosage is 6 mg/head, and the obtained diluted solution was injected into the abdominal cavity of the mice in group J by 1 mg every other day after the first immunity.

Chinese licorice extract obtained in Comparative Example 2 was diluted by physiological saline so that the dosage is 12.5 mg/head, and the obtained diluted solution was injected into the abdominal cavity of the mice in group K by 1 mg every other day after the first immunity.

Prednisolone acetate (produced by Shionogi & Co., Ltd.) which is a control drug was suspended by physiological saline so that the dosage is 5 mg/Kg of body weight, and the obtained suspended solution was injected into the abdominal cavity of each mouse in group L by 1 ml every other day after the first immunity.

The above injections were performed all through the test period (for eight weeks after the first immunity).

IV. Weight Measurement of Mice

The weight of the mice in the respective groups were measured every day after the first immunity and the average weight per each of the groups was calculated. The results are shown in FIG. 2.

Figure 2:
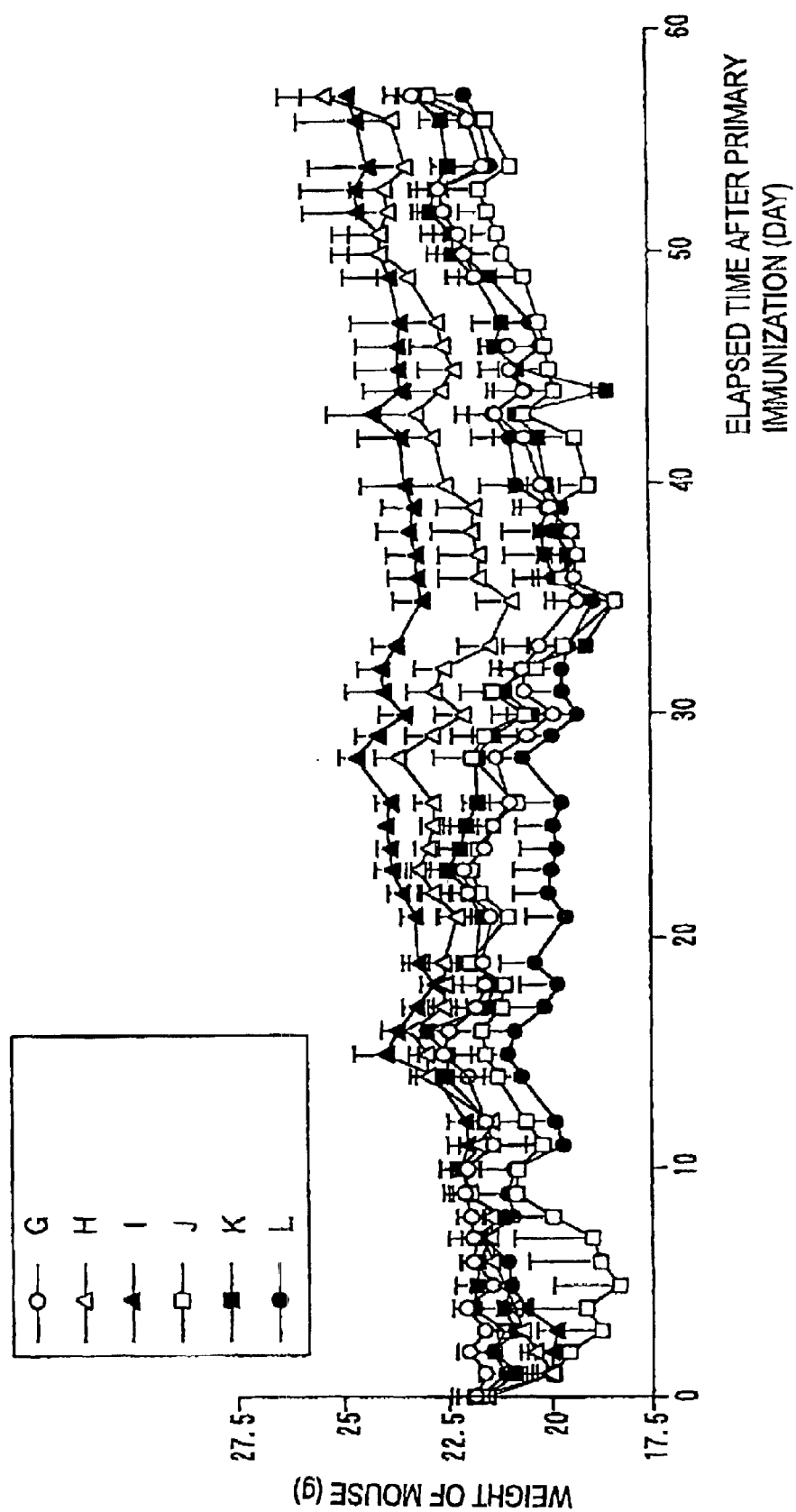
FIG. 2 is an explanatory diagram showing weight changes of mice in an experiment 2.

As can be seen from FIG. 2, there was no visible reduction of average weight in the mice of groups H and I to which Brazilian licorice extract was injected. In addition, there was no reduction in average weight in the mice of groups H and I after the second immunity, either.

On the other hand, the average weights of the mice in group G without drug injection, groups J and K to which Chinese licorice extract was injected, and group K to which prednisolone acetate was injected were reduced significantly compared to the average weights of mice in groups H and I.

V. Accordingly, Brazilian licorice extract hardly causes side effects and is highly secure compared to Chinese licorice extract and prednisolone acetate.

Evaluation of Arthritis Condition (Arthritis Index)

Clinical symptoms of arthritis of mice in the respective groups were evaluated by one and the same observer using 6 rankings from zero to five (the larger the value is, the worse the symptom is), and the averages per the respective groups were calculated. These evaluations were performed in 0, $3^{rd}$, $4^{th}$, $5^{th}$, $6^{th}$, $7^{th}$ and $8^{th}$ week after the first immunity The results were shown in FIG. 3 and Table 3. In Table 3, values in the upper section show the average in the respective groups, and the values in the lower section show the standard deviation.

TABLE 3

| Drug type | Gr. | Dosage | Primary immunity | 3rd week | 4th week | 5th week | 6th week | 7th week | 8th week |
|---|---|---|---|---|---|---|---|---|---|
| None | G | — | 0 | 0.688 | 1.313 | 3.125 | 2.688 | 2.688 | 2.688 |
| | | | 0 | 0.377 | 0.4 | 0.611 | 0.582 | 0.49 | 0.462 |
| B.L. | H | 6 mg/head | 0 | 0 | 0.25 | 1.625 | 1.625 | 0.938 | 0.929 |
| | | | 0 | 0 | 0.189 | 0.653 | 0.673 | 0.29 | 0.254 |
| | I | 12.5 mg/head | 0 | 0 | 0 | 0.9 | 1.2 | 0.8 | 0.6 |
| | | | 0 | 0 | 0 | 0.9 | 0.846 | 0.339 | 0.367 |
| C.L. | J | 6 mg/head | 0 | 0 | 0.5 | 2.833 | 2.75 | 2.583 | 2.167 |
| | | | 0 | 0 | 0.5 | 0.843 | 0.588 | 0.396 | 0.307 |
| | K | 12.5 mg/head | 0 | 0 | 0.571 | 3 | 3.071 | 3.071 | 2.357 |
| | | | 0 | 0 | 0.277 | 0.556 | 0.539 | 0.297 | 0.404 |
| Pred. | L | 5 mg/head | 0 | 0 | 0 | 0 | 0 | 0.125 | 0.125 |
| | | | 0 | 0 | 0 | 0 | 0 | 0.125 | 0.125 |

Figure 3:
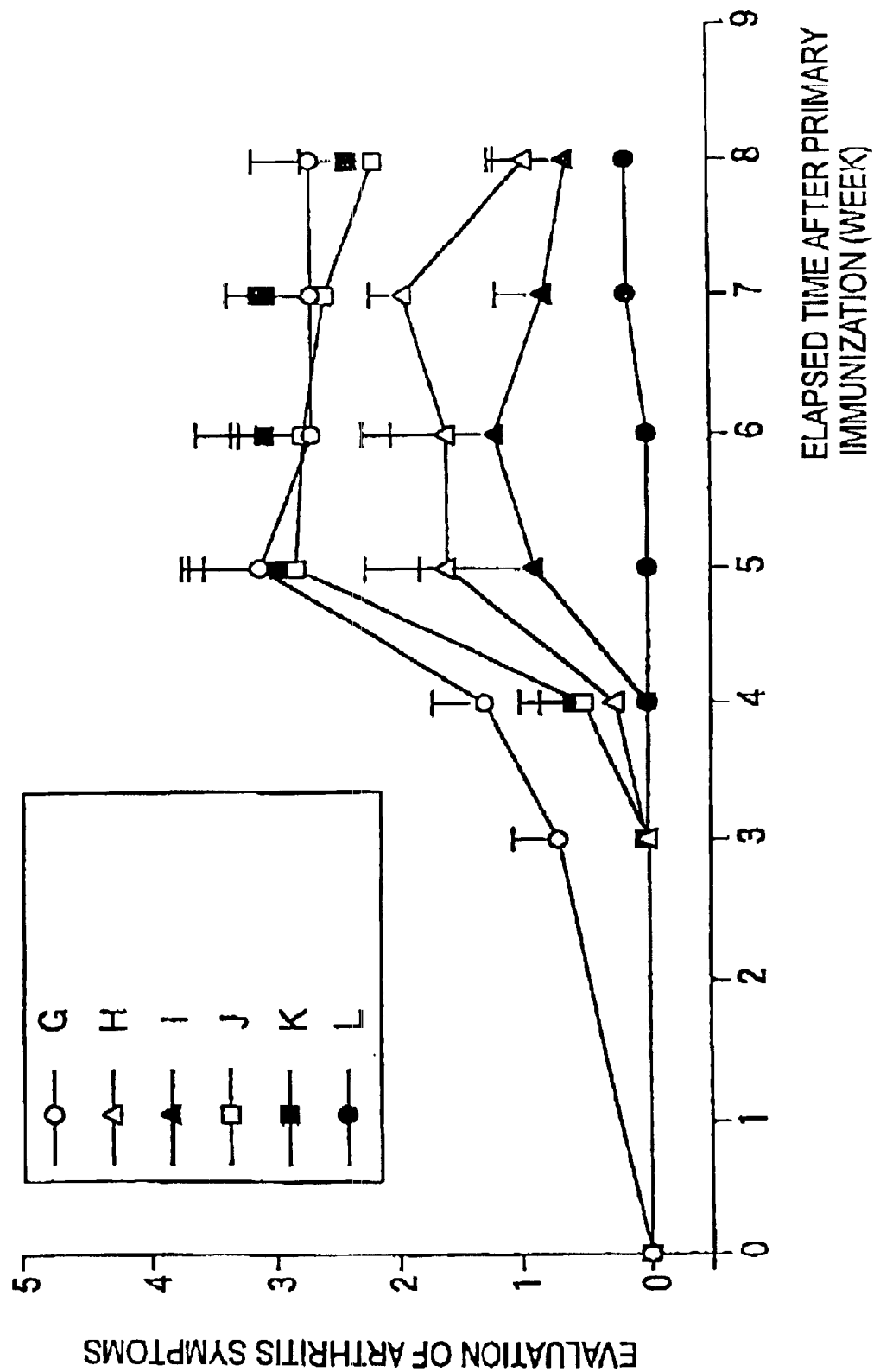
FIG. 3 is an explanatory diagram showing changes in evaluation values of arthritis in the experiment 2.

As can be seen from FIG. 3 and Table 3, the arthritis symptoms of mice in groups to which Brazilian licorice extract was injected (groups H and I) were improved compared to the mice in group G without drug injection and groups J and K to which Chinese licorice extract was injected.

In view of the above, it is clear that Brazilian licorice extract has superior anti-inflammatory and immunosuppressive effects to Chinese licorice extract.

As to the mice in groups H and I to which Brazilian licorice extract was injected, the symptoms of the mice in group I to which large quantity (12.5 mg/head) of the extract was injected per one time were better improved than the mice in group H to which small quantity (6 mg/head) of the extract was injected per one time. In short, the effect of improving arthritis symptoms by Brazilian licorice extract showed dose dependency.

VI. Measurement of Foot Pad Swelling (Foot Pad Volume)

Figure 4:
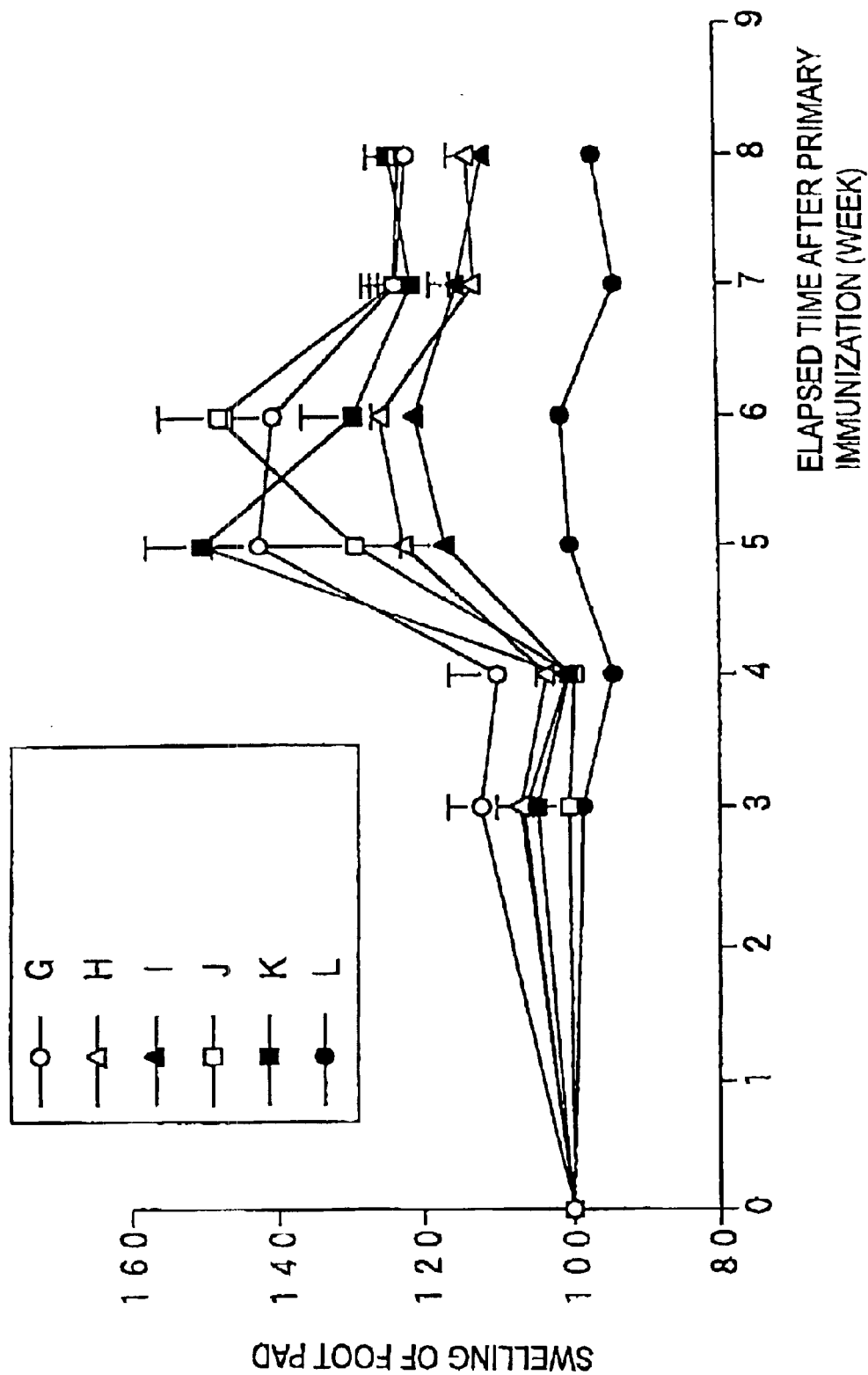
FIG. 4 is an explanatory diagram showing changes in foot pad swelling in the experiment 2.

The left and right hind foot pad volumes of the mice in the respective groups were measured using a plethysmometer (TK-101 UNICOM), and the average per each of the groups was calculated. These evaluations were performed in 0, $3^{rd}$, $4^{th}$, $5^{th}$, $6^{th}$, $7^{th}$ and $8^{th}$ weeks after the first immunity. The results were shown in FIG. 4 and Table 4. The values in FIG. 4 are relative values based on the initial hind foot pad volumes. In Table 4, the values in the upper section show the averages of the respective groups and the values in the lower section show the standard deviation.

It is clear from FIG. 4 and Table 4 that there was a superior effect of inhibiting foot pad swelling in the mice in groups H and I to which Brazilian licorice extract was injected compared to the mice in group G without drug injection and groups J and K to which Chinese licorice extract was injected.

It should be noted that a superior effect of inhibiting foot pad swelling was seen even in the mice in group I to which less Brazilian licorice extract (6 mg/head) was injected compared to the mice in groups G, J and K.

In view of the above, Brazilian licorice extract has superior anti-inflammatory and immunosuppressive effects to Chinese licorice extract.

Experiment 3

Anti-inflammatory effect and immunosuppressive effect of the extract obtained in Example 2 and Comparative Example 2 were examined by autoimmune encephalomyelitis model experiment using rats.

I. Preparation of Rats to be Used in Experiment

Eight weeks old male rats of DA system were used in the experiment. The rats were divided into 6 groups, namely, M, N, O, P, Q and R, each consisting of six rats.

II. Induction of Autoimmune Encephalomyelitis by Injection of Emulsion to Rats

An equal amount of 2 mg/ml concentration of a bovine Myeline Basic Protein (MBP) solution (the solvent is phosphate buffered saline) and fetal bovine serum containing supersonically treated 4 mg/ml Microbacterium tuberculosis H37Ra were mixed to prepare emulsion.

50 µl of the emulsion was then injected hypodermically to hind leg foot pads of the respective rats under ether (in other

TABLE 4

| Drug type | Gr. | Dosage | Primary immunity | 3rd week | 4th week | 5th week | 6th week | 7th week | 8th week |
|---|---|---|---|---|---|---|---|---|---|
| None | M | — | 100 | 112.9 | 111 | 143.3 | 141.2 | 124.7 | 122.7 |
| | | | 0 | 4.517 | 6.084 | 6.821 | 5.534 | 3.109 | 2.241 |
| B.L. | N | 6 mg/head | 100 | 107.9 | 104 | 123.1 | 126.4 | 114 | 114.7 |
| | | | 0 | 1.34 | 1.871 | 6.793 | 5.543 | 3.117 | 2.509 |
| | O | 12.5 mg/head | 100 | 107.3 | 101 | 117.8 | 121.7 | 116 | 112.4 |
| | | | 0 | 3.588 | 2.527 | 6.113 | 6.04 | 3.417 | 2.478 |
| C.L. | P | 6 mg/head | 100 | 100.9 | 100.7 | 130 | 148.6 | 124.6 | 123.4 |
| | | | 0 | 3.644 | 4.638 | 12.752 | 8.55 | 4.338 | 4.846 |
| | Q | 12.5 mg/head | 100 | 105.4 | 101.5 | 150.8 | 130.7 | 122.2 | 124.4 |
| | | | 0 | 1.287 | 3.145 | 7.663 | 6.619 | 4.528 | 4.313 |
| Pred. | R | 5 mg/head | 100 | 99.2 | 95.2 | 101.1 | 102.4 | 95.5 | 97.9 |
| | | | 0 | 2.328 | 2.037 | 2.347 | 1.866 | 1.615 | 1.692 | words, 100 μl (100 μgMBP/head) was injected per rat), to induce autoimmune encephalomyelitis.

III. Injection of Brazilian Licorice Extract and Comparative Sample

A solvent without drugs was injected into the rats in group M.

Brazilian licorice extract obtained in Example 2 was diluted by physiological saline so that the dosage is 25 mg/head, and the obtained diluted solution was injected into the abdominal cavity of the rats in group N by 1 ml once a day for 12 consecutive days after the injection of emulsion.

Brazilian licorice extract obtained in Example 2 was diluted by physiological saline so that the dosage is 50 mg/head, and the obtained diluted solution was injected into the abdominal cavity of the rats in group O by 1 ml once a day for 12 consecutive days after the injection of emulsion.

Chinese licorice extract obtained in Comparative Example 2 was diluted by physiological saline so that the dosage is 25 mg/head, and the obtained diluted solution was injected into the abdominal cavity of the rats in, group P by 1 ml once a day for 12 consecutive days after the injection of emulsion.

Chinese licorice extract obtained in Comparative Example 2 was diluted by physiological saline so that the dosage is 50 mg/head, and the obtained diluted solution was injected into the abdominal cavity of the rats in group Q by 1 ml once a day for 12 consecutive days after the injection of emulsion.

Prednisolone acetate (produced by Shionogi & Co., Ltd.) which is a control drug was suspended by physiological saline so that the dosage is 5 mg/Kg of body weight, and the obtained suspended solution was injected into the abdominal cavity of each rat in group R by 1 ml once a day for 12 consecutive days after the injection of emulsion.

IV. Evaluation of Encephalomyelitis (Clinical Score)

After the injection of emulsion, the rats in the respective groups were observed every day to evaluate symptoms of encephalomyelitis (Clinical sore). The symptoms were evaluated by six rankings from zero to five (the larger the value, the worse the symptom is) according to the criteria shown in Table 5, and the averages per the respective groups were calculated. The above observations were conducted for 25 consecutive days after the injection of emulsion.

TABLE 5

| Value | Criteria of clinical score of encephalomyelitis |
|---|---|
| 0 | No change |
| 1 | Paralysis of tail |
| 2 | Incomplete paralysis of hind legs |
| 3 | Complete paralysis of hind legs and incomplete paralysis of front legs |
| 4 | Paralysis of limbs, incontinence |
| 5 | Dead |

Figure 5:
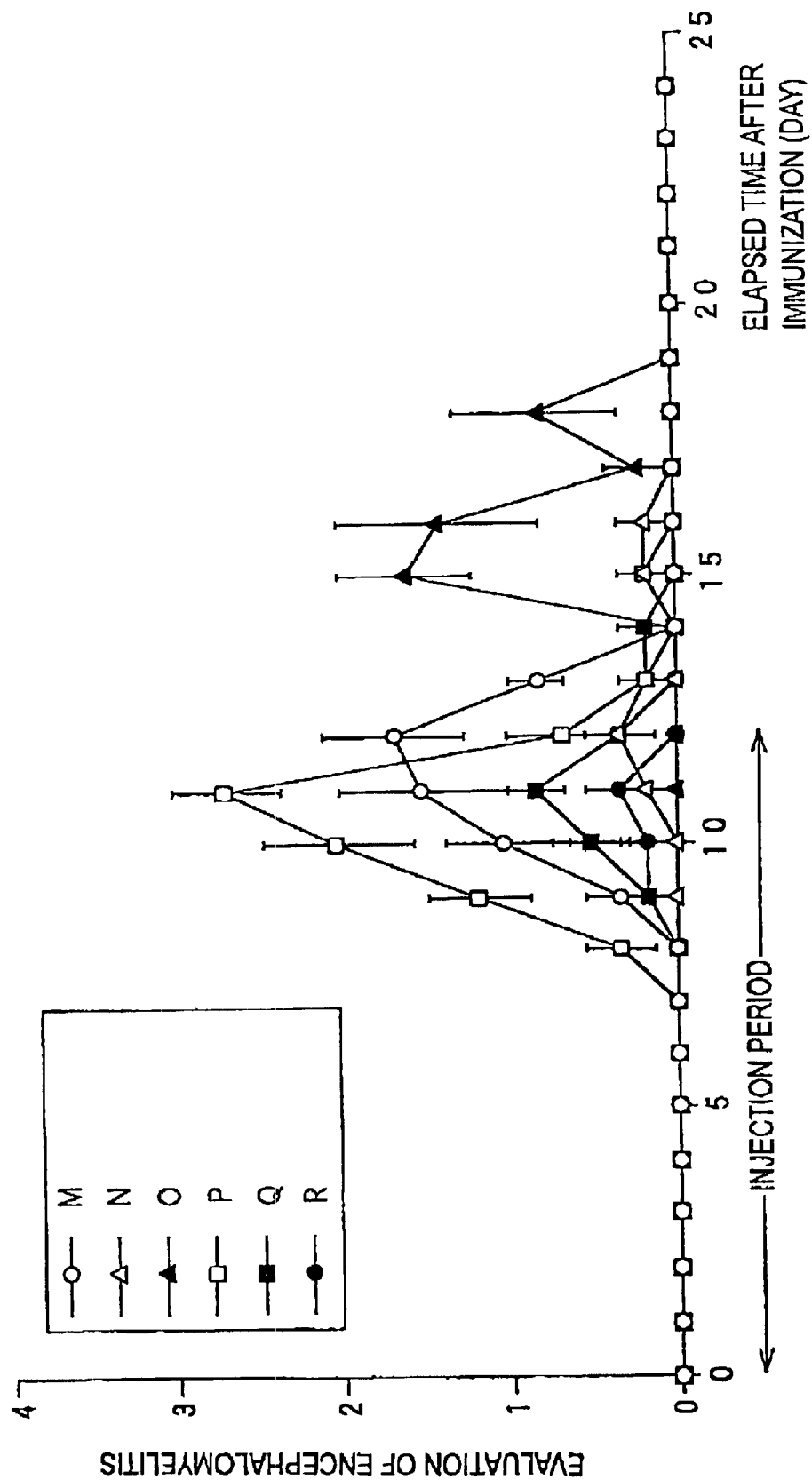
FIG. 5 is an explanatory diagram showing changes in evaluation values of encephalomyelitis in an experiment 3.

The results of the evaluation are shown in FIG. 5. As can be clearly seen from FIG. 5, a few rats in group N to which 25 mg/head of Brazilian licorice extract was injected developed encephalomyelitis during and after the injections. However, most of the rats did not develop encephalomyelitis.

The mice in group O to which 50 mg/head of Brazilian licorice extract was injected did not develop encephalomyelitis during the injections at all. However, they developed encephalomyelitis after the injections were completed.

On the other hand, the rats in group M without drug injection was and groups P and Q to which Chinese licorice extract was injected developed encephalomyelitis 7–8 days after the injection of emulsion. The symptoms reached its peak on $11^{th}$–$12^{th}$ days and were disappeared on $14^{th}$ day. The symptoms of the rats in group Q to which more Chinese licorice extract was injected (50 mg/head) were slightly better than the rats in groups M and P.

A few rats in group R to which prednisolone acetate was injected developed encephalomyelitis 8–11 days after the injection of emulsion.

In view of the above, Brazilian licorice extract has superior anti-inflammatory and immunosuppressive effects to Chinese licorice extract.

Experiment 4

The immunosuppressive effect of the BL. 1, BL. 2 and BL. 3, which are fractionated components of Brazilian licorice extract obtained in Example 3, was examined by autoimmune encephalomyelitis model experiment using rats.

The manner of experiment was basically the same as the aforementioned Experiment 3.

However, the number of groups of rats were reduced to five, one of which included the rats to which the BL. 1 was injected, another of which included the rats to which the BL. 2 was injected, another of which included the rats to which the BL. 3 was injected, another of which included the rats to which prednisolone acetate was injected, and another of which included the rats without injection.

The dose per one injection of BL. 1, BL. 2 and BL. 3 was 6 mg/head and in the form of physiological saline.

The dose per one injection of prednisolone acetate was 5 mg/Kg of body weight and in the form of physiological saline.

Figure 6:
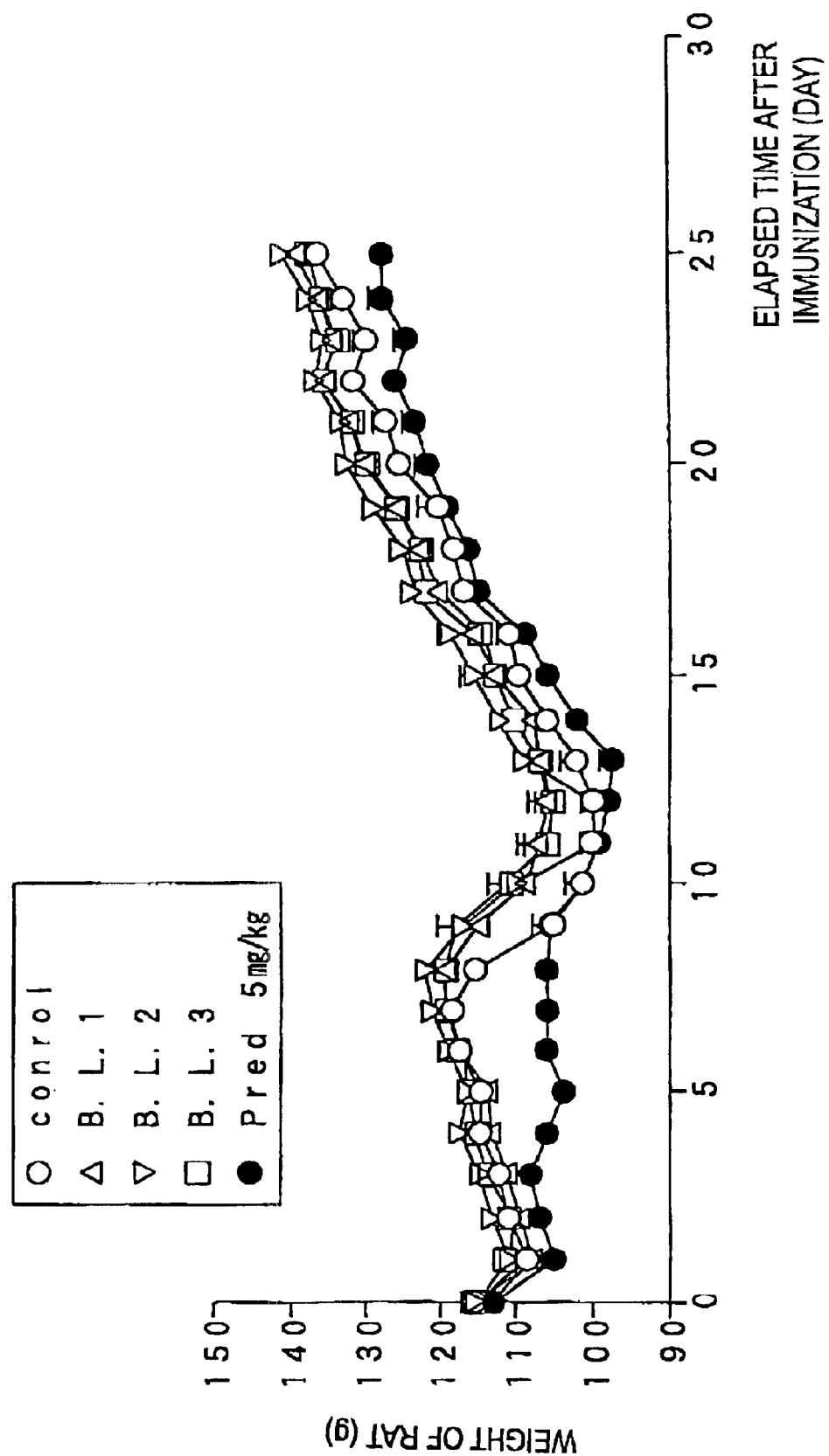
FIG. 6 is an explanatory diagram showing weight changes of mice in an experiment 4.

FIG. 6 shows weight changes of the rats in the respective groups during the experiment period.

The rats in the groups to which the BL. 1, BL. 2 and BL. 3 were injected gained about additional 5–10 g compared to the rats in the control group on and after $8^{th}$ day after the immunity.

The rats in the group to which prednisolone acetate was injected had the least increase among the rats in the other groups.

Figure 7:
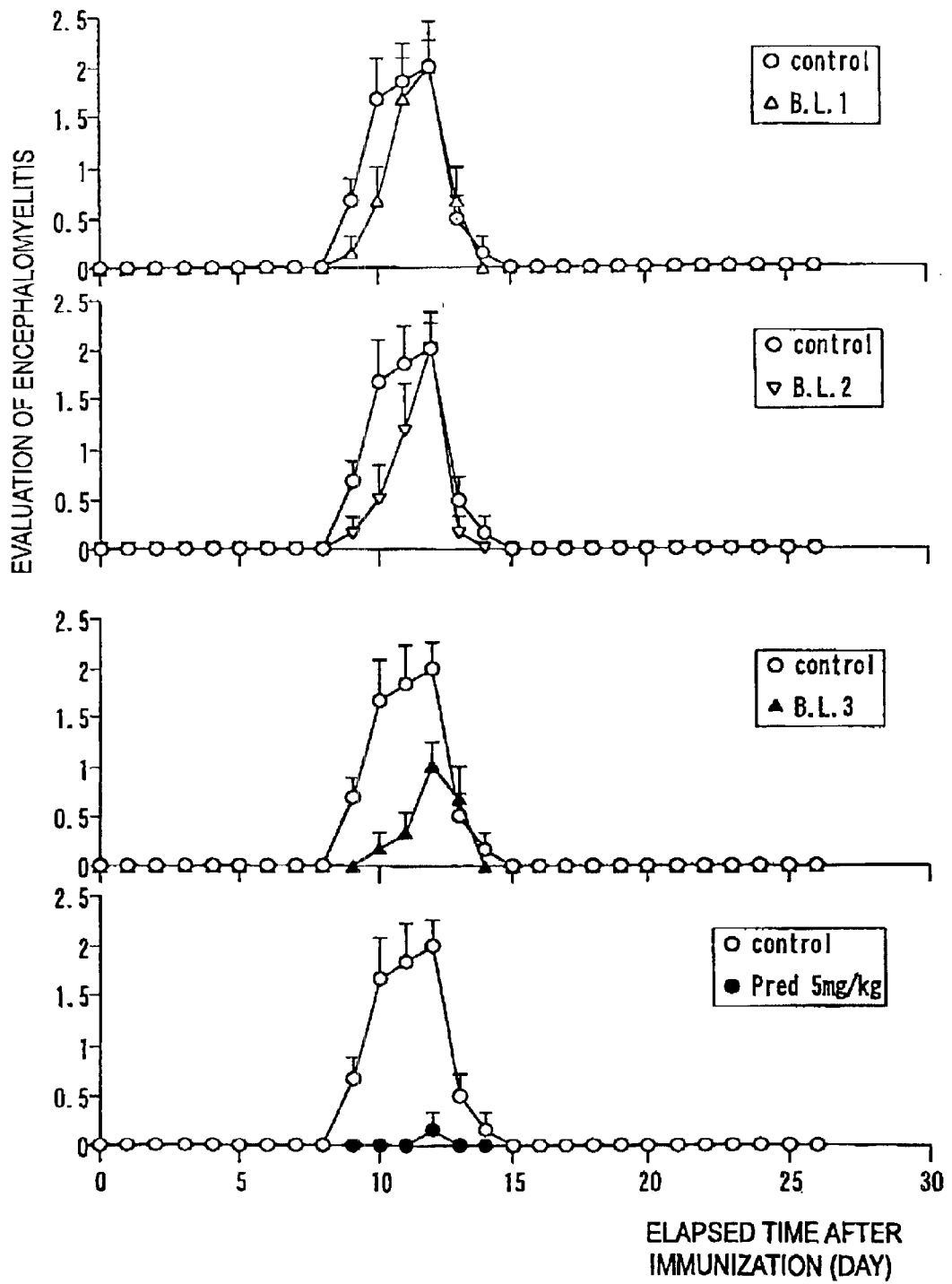
FIG. 7 is an explanatory diagram showing changes in evaluation values of encephalomyelitis in the experiment 4.
Figure 8:
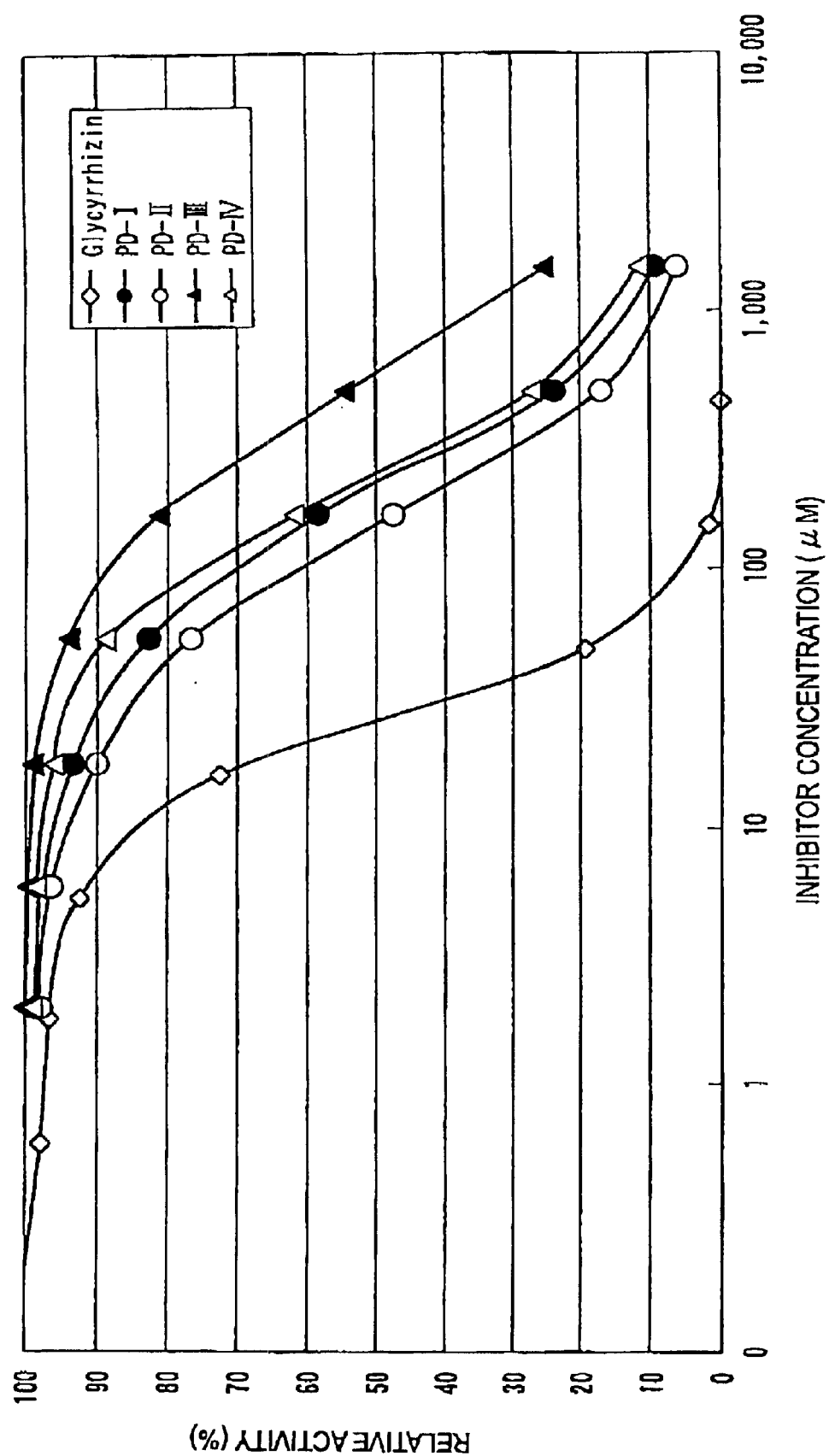
FIG. 8 is an explanatory diagram contrastively showing an effect of inhibiting hydroxysteroid dehydrogenase activation as a side effect in an experiment 5.

FIG. 7 shows the evaluation results on encephalomyelitis. The evaluation criteria are the same as the above Table 5.

Development of encephalomyelitis was strongly inhibited in the rats to which the BL. 3 was injected compared to any of the rats in the groups to which the BL. 1 and BL. 2 were injected, and the rats in the control group. Development of encephalomyelitis was slightly inhibited in the rats to which the BL. 2 was injected compared to the rats in the control group.

In addition, there was no temporary development (for example, development caused on $15^{th}$–$16^{th}$ days in the rats of group O in Experiment 3) after completion of the injections in the rats in the group to which the BL. 3 was injected.

The results of Experiment 4 indicate that not the component contained in the BL. 1 (polar component such as polysaccharide which is not held by suction chromatography carrier such as HP-20), but the polar component such as triterpenoid glycoside (for example, periandrins) contained in the BL. 3 has an immunosuppressive effect.

Experiment 5

In order to evaluate the effect of inhibiting 11 β-hydeoxysteroid dehydrogenase activity by the purified periandrins (PD-I, PD-II, PD-III, PD-IV) obtained in Example 4 or 5, IC 50 values (concentration in which the 50 percent of activity of the above enzyme is inhibited) of the purified periandrins were measured by the following steps I–VI.

Note that inhibition of 11 β-hydroxysteroid dehydrogenase activity is considered to be a cause of pseudoaldosteronism.

I. An enzymatic solution containing rat liver microsome as a preparation of 11 β-hydroxysteroid dehydrogenase was prepared as below.

Fresh rat liver was ice-cooled and homogenized in 0.25 M sucrose solution. Then, at the temperature of 4° C., it was centrifuged for 20 minutes at 10,000×g.

After separating cell organelles of the nucleus, mitochondria and lysosome as deposits, the supernatant layer was further centrifuged at 105,000×g for 60 minutes at the temperature of 4° C. to obtain a microsome fraction as a precipitate.

The obtained microsome fraction was suspended by 0.25 M sucrose solution to produce an enzymatic solution, and the obtained solution was stored at the temperature of −20 degrees till the time of measurement of enzyme activity.

II. Measurement of Enzyme Activity 1 mM of NADP (product of Oriental Yeast Co., Ltd,) as a coenzyme and an amount of PD-I having a predetermined concentration (ranging from 2 to 1480 $\mu$M) as an inhibitor were added to 0.8 ml of Tris-HCl buffer solution having the concentration of 100 mM (PH8.0).

0.2 ml of the enzymatic solution prepared in step I was added to the obtained solution, and after three minutes of preincubation at 37° C., 0.02 ml of 5 mM hydrocortisone solution which was dissolved in methanol was added to start a reaction between 11 β-hydroxysteroid dehydrogenase and PD-I. The reaction was continued for 30 minutes at the temperature of 30° C., and then it was stopped by adding 0.5 ml of ethyl acetate.

This solution was centrifuged and an ethyl acetate layer was separated into an Eppendorf tube. In the mean time, cortisone and substrate hydrocortisone generated by the reaction between 11 β-hydroxysteroid dehydrogenase and substrate hydrocortisone are transferred to the ethyl acetate layer.

Furthermore, the water phase after the centrifuge was again centrifuged in the same manner as above by adding 0.5 ml of ethyl acetate to separate an ethyl acetate layer. This process was repeated two more times.

The ethyl acetate layers obtained by three time extraction were put together into an Eppendorf tube and dried using a centrifugal evaporator.

III. Determination of Generated Cortisone

To prepare a measurement sample, 0.2 ml of methanol was added into the Eppendorf tube in which the ethyl acetate layers were dried in step II, and then the tube was left for a night so that cortisone was completely dissolved. Cortisone was determined using HPLC.

Particularly, quantity of cortisone contained in the sample was calculated from a ratio of a peak area corresponding to cortisone when the measurement sample was introduced to HPLC to a peak area when 5 $\mu$l of standard solution (0.1 mg/ml of cortisone-methanol solution) was introduced.

The measurement conditions of HPLC were as follows.

| | |
|---|---|
| Stationary phase: | NovaPak cartridge C18, 3.9 × 150 mm (product of Japan Waters) |
| Moving phase: | 45% methanol solution containing 0.1% trifluoroacetic acid (isocratic) |
| Flow rate: | 0.5 ml/min |
| Detection: | UV 245 nm |
| Injection amount: | 5 $\mu$l |

IV. Relative activity (ratio of activity remained after reaction with an inhibitor to the initial activity) of 11 β-hydroxysteroid dehydrogenase was calculated from the quantity of cortisone in accordance with the following equation.

$$\text{Relative activity} = ((C_I - C_{BL})/(C_T - C_{BL})) \times 100 (\%)$$

where $C_T$: cortisone quantity generated when no inhibitor is added;

$C_I$: cortisone quantity generated when an inhibitor exists; and $C_{BL}$: cortisone quantity when enzyme is not added.

V. Measurement of relative activity when PD-II, PD-III, PD-IV, and glycirrhizin were added as an inhibitor instead of PD-I was performed in the same manner as in steps I–IV.

The concentration of the inhibitor PD-I, PD-II, PD-III or PD-IV in the measurement of relative activity is a predetermined value ranging from 2 to 1480 $\mu$M. The concentration of glycirrhizin is a predetermined value ranging from 0.2 to 445 $\mu$M.

The system to which no inhibitor was added was considered as a control, and the system to which no substrate was added is considered as a blank.

VI. As shown in FIG. 6, relation between the concentrations of the respective inhibitors and the relative activity was plotted, and the inhibitor concentration of which relative activity is equal to 50% was made IC50 of the inhibitor.

As to the measurement results, on one hand, the IC50 value of glycirrhizin was 26.2 $\mu$M, and on the other hand, the IC50 values of PD-I, PD-II, PD-III and PD-IV were respectively 214 $\mu$M, 150 $\mu$M, 581 $\mu$M, 240 $\mu$M, which were high in one order.

In other words, inhibitory activity of PD-I, PD-II, PD-III and PD-IV was about one fifth to one twentieth of glycirrhizin.

Accordingly, since the purified periandrins hardly inhibit 11 β-hydroxysteroid dehydrogenase activity, pseudoaldosteronism, which is considered to be caused by inhibition of 11 β-hydroxysteroid dehydrogenase activity, is not developed by using the products comprising the purified periandrins (cytokine production inhibitors, agents for protecting and promoting liver function, anti-inflammatory agents, immunosuppressants, drugs, cosmetics, foods and food materials).

Experiment 6

The effects of inhibiting cytokine production and of protecting and promoting liver function with respect to PD-I, PD-II, PD-III and PD-IV obtained in Example 4 or 5 were examined in the same manner as in Experiment 1.

In this case, however, the number of groups of rats were made six, one of which includes the rats to which PD-I was injected, another of which includes the rats to which PD-II was injected, another of which includes the rats to which PD-III was injected, another of which includes the rats to which PD-IV was injected, another of which includes the rats to which prednisolone acetate was injected, and another of which includes the rats to which a solvent without any drugs was injected.

The dose per one injection of PD-I, PD-II, PD-III and PD-IV was 0.1–3 mg/Kg of body weight.

The dose per one injection of prednisolone acetate was 5 mg/Kg of body weight.

All of PD-I, PD-II, PD-III and PD-IV show the effects of inhibiting cytokine production and protecting and promoting liver function. It was found that these components are at least one part of the active ingredient of Brazilian licorice extract.

Furthermore, the collagen induction arthritis model experiment and autoimmune encephalomyelitis model experiment shown in Experiments 2 and 3 were applied using PD-I, PD-II, PD-III and PD-IV obtained in Experiment 4. As a result, these components eased the symptoms of arthritis and encephalomyelitis like Brazilian licorice extract did.

From the above, the purified periandrins (PD-I, PD-II, PD-III and PD-IV) have anti-inflammatory effect and immunosuppressive effect.

The present invention should not be limited to the described embodiments, and other modifications and variations might be possible without departing from the scope of the invention.

For example, in the process of obtaining Brazilian licorice extract, the solvent is not limited to ethanol, but other solvents (e.g. water, alcohols such as methanol, isopropanol, isobutanol, hexanol, methyl amyl alcohol, 2-ethyl butanol, n-octyl alcohol, etc., polyhydric alcohols and the derivatives such as glycerin, ethylene glycol, ethylene glycol monomethyl ether, ethylene glycol monoethyl ether, propylene glycol, propylene glycol monomethyl ether, propylene glycol monoethyl ether, triethylene glycol, 1,3-butylene glycol, hexylene glycol, etc., ketones such as acetone, methyl ethyl ketone, methyl isobutyl ketone, etc., esters such as ethyl acetate, isopropyl acetate, etc., ethers such as ethylether, isopropylether, n-bytylether, etc., aliphatic hydrocarbons such as petroleum ether, n-hexane, n-pentane, n-butane, n-octane, cyclohexane, etc., and non polar solvents such as tetrachloromethane, chloroform, trichloroethylene, benzol, toluene, etc.) can be used.

INDUSTRIAL APPLICABILITY

By adopting Brazilian licorice extract or periandrins as a cytokine production inhibitor, it is possible to inhibit inflammation of various diseases such as rheumatoid arthritis. Brazilian licorice extract and periandrins can be used as an agent for protecting and promoting liver function, an anti-inflammatory agent, and an immunosuppressant. Furthermore, foods, cosmetics, sweeteners and food materials comprising Brazilian licorice extract also have the same effect as above.

What is claimed is:

1. A method of treating an inflammatory condition in a mammalian patient in need of such treatment, comprising administering to the patient one or more periandrins in an amount effective as an anti-inflammatory.

2. The method of treating an inflammatory condition as set forth in claim 1, wherein the one or more periandrins are administered as a pharmaceutical composition comprising purified Brazilian licorice extract containing periandrins in a pharmaceutically acceptable carrier or diluent.

3. The method of treating an inflammatory condition as set forth in claim 2, wherein the one or more periandrins are in substantially pure form.

* * * * *